United States Patent [19]
Lancini et al.

[11] Patent Number: 5,925,550
[45] Date of Patent: Jul. 20, 1999

[54] METHOD FOR SELECTIVELY INCREASING THE RATIO OF SINGLE MAJOR COMPONENTS OF ANTIBIOTIC A/16686 COMPLEX

[75] Inventors: Giancarlo Lancini, Pavia; Angelo Borghi, Milan; Piero Antonini, Arluno, all of Italy

[73] Assignee: Biosearch Italia S.p.A., Italy

[21] Appl. No.: 08/993,729

[22] Filed: Dec. 18, 1997

Related U.S. Application Data

[63] Continuation of application No. 08/457,607, Jun. 1, 1995., abandoned, which is a continuation of application No. 08/267,094, Jun. 28, 1994., abandoned, which is a continuation of application No. 08/141,426, Oct. 22, 1993., abandoned, which is a continuation of application No. 07/866,072, Apr. 1, 1992., abandoned, which is a continuation of application No. 07/519,333, May 2, 1990., abandoned, which is a continuation of application No. 07/095,364, Sep. 10, 1987., abandoned

Foreign Application Priority Data

Sep. 11, 1986 [GB] United Kingdom .................... 8621911

[51] Int. Cl.⁶ ................................ C12P 21/04; C12N 1/38
[52] U.S. Cl. ............................ 435/71.3; 435/74; 435/75; 435/76; 435/127; 435/244; 435/169
[58] Field of Search ................................ 435/74, 75, 71.3, 435/76, 127, 244, 169

[56] References Cited

U.S. PATENT DOCUMENTS

| | | |
|---|---|---|
| 4,427,656 | 1/1984 | Cavalleri et al. ....................... 435/169 |
| 5,108,988 | 4/1992 | Ciabatti et al. . |
| 5,491,128 | 2/1996 | Ciabatti et al. . |
| 5,539,087 | 7/1996 | Restelli et al. . |

FOREIGN PATENT DOCUMENTS 0204197  12/1986  European Pat. Off. .

OTHER PUBLICATIONS

Ciabatti et al., The Journal of Antibiotics, vol. XLII No. 2, Feb., 1989, pp. 254–267.

*Primary Examiner*—Irene Marx
*Attorney, Agent, or Firm*—Killworth, Gottman, Hagan & Schaeff, LLP

[57] ABSTRACT

The present invention relates to a method for selectively enhancing the production of factors $A_2$ and/or $A_3$ of antibiotic A/16686 either to isolate these single components or to enrich the complex in one or both the above components, which comprises adding an appropriate precursor of the desired antibiotic factor to an A/16686 producing culture during fermentation.

36 Claims, No Drawings

METHOD FOR SELECTIVELY INCREASING THE RATIO OF SINGLE MAJOR COMPONENTS OF ANTIBIOTIC A/16686 COMPLEX

This application is a continuation of application Ser. No. 08/457,607, filed Jun. 1, 1995 now abandoned, which is a continuation of application Ser. No. 08/267,094, filed Jun. 28, 1994, now abandoned, which is a continuation of application Ser. No. 08/141,426, filed Oct. 22, 1993, now abandoned, which is a continuation of application Ser. No. 07/866,072, filed Apr. 1, 1992, now abandoned, which is a continuation of application Ser. No. 07/519,333, filed May 2, 1990, now abandoned, which is a continuation of application Ser. No. 07/095,364, filed Sep. 10, 1987, now abandoned which is herein incorporated by reference.

Antibiotic A/16686 is a depsipeptidic substance isolated from a culture of Actinoplanes sp. ATCC 33076.

This substance, which is mainly active against gram positive bacteria, has been described in U.S. Pat. No. 4,303,646 together with the process for obtaining it and the corresponding pharmaceutical compositions.

It was then found that three closely related components could be isolated from antibiotic A/16686 which were named factor $A_1$, $A_2$, and $A_3$. Factor $A_2$ is the component obtained in preponderant amount and is the most relevant for the biological activity, while factors $A_1$ and $A_3$ are obtained in a minor amount. These substances as well as their preparation and uses are described in U.S. Pat. No. 4,427,656. The chemical structure of these factors is given by R. Ciabath et al, *The Journal of Antibiotics*, 42(2), 254–67 (1989).

Due to the increasing development of tolerance and even resistance to current antibiotic treatments, the need for new antibiotic substances is still high.

Particularly desirable are antibiotics in single isolated form or complex with very well defined and standardized composition.

One object of the invention is therefore a method for selectively enhancing the production of factors $A_2$ and/or $A_3$ of antibiotic A/16686 either to isolate these single components or to enrich the complex in one or both the above components, which comprises adding an appropriate precursor of the desired antibiotic factor to an A/16686 producing culture during fermentation.

According to the method of the invention, it is in fact possible, for instance, to modulate the ratio of the single major components of antibiotic A/16686 complex in large scale industrial fermentation. This method therefore represents a useful tool to adjust the composition of the final product to adhere to standard specifications.

Moreover, by following the procedure of the invention it is also possible to obtain, directly from the fermentation mass of the producing strain, a crude product very rich in antibiotic A/16686 factor $A_2$ which can then be isolated in a pure form with higher yields and less time consuming steps.

The appropriate precursor for increasing the ratio of factor $A_2$ in antibiotic A/16686 complex is selected from leucine, its salts with acids and bases which are non-toxic to the producing microorganism, isovaleric acid, its salts with bases which are non-toxic to the producing microorganism, its esters with mono- and poly-hydroxy lower alkanols, alpha-keto-isocaproic acid, its salts with bases which are non-toxic to the producing microorganism, its esters with mono- and poly-hydroxy lower alkanols, isoamyl alcohol and its esters with acids which are non-toxic to the producing microorganism.

The appropriate precursor for increasing the ratio of factor $A_3$ in antibiotic A/16686 complex is selected from valine, its salts with acid and bases which are non-toxic to the producing microorganism, alpha-keto-isovaleric acid, its salts with bases which are non-toxic to the producing microorganism, its esters with mono- and poly-hydroxy lower alkanols, isobutyric acid, its salts with bases which are non-toxic to the producing microorganism, its esters with mono- and poly-hydroxy lower alkanols, isobutanol and its esters with acids which are non-toxic to the producing microorganism.

Salts with bases which are non-toxic to the microorganism are salts wherein the type and concentration of the given cation is such that it does not impair either the growth of the microorganism culture or the production of the desired antibiotic substance to a considerable extent at the concentration employed in the fermentation mass. Examples of said cations are those from alkali metals and alkaline earth metals such as sodium, potassium, calcium or magnesium, as well as those from amines, such as ammonium, primary, secondary or tertiary ($C_1$–$C_4$) alkyl ammonium and hydroxy ($C_1$–$C_4$) alkyl ammonium. Preferred salts are those with sodium, potassium or ammonium ions.

Examples of salts with acids which are non-toxic to the producing microorganism, i.e. salts with acids which do not either impair considerably the growth of the microorganism culture or the production of the desired antibiotic substance, at the concentration at which they are present in the fermentation mass, are preferably mineral acids such as hydrochloric acid, even if also organic acids may, in some instances, be present.

Esters of an appropriate precursor as defined above with mono- and poly-hydroxy lower alkanols are esters with ($C_1$–$C_6$) alkanols with 1, 2, 3, 4, 5, or 6 hydroxy functions per molecule. When ($C_1$–$C_4$) alkanols are used, they must be different from those which act as precursors for the other antibiotic factor (i.e. isobutanol or isoamyl alcohol) unless concomitant increase of both factors is desired.

Preferred examples of poly-hydroxy alkanols are glycerol and propylene gylcol.

When the lower alkanol may be present in different enantiomeric and epimeric forms, in the present description and claims, each single form separately as well as the mixture of said single form in any proportion is intended.

Esters of an appropriate hydroxy containing precursor as defined above which are non-toxic to the microorganism are ($C_2$–$C_{22}$) alkanoyl esters wherein the type and concentration of the alkanoyl moiety in the fermentation medium is such that it does not impair the growth of the microorganism culture or the production of the desired antibiotic substance to a considerable extent. In general, straight chain ($C_2$–$C_4$) alkanols are preferred.

An antibiotic A/16686 producing culture is a culture of a strain like Actinoplanes sp. ATCC 33076, or a producing mutant or variant thereof, which is capable, upon cultivation, of producing recoverable amounts of antibiotic A/16686.

The method of the invention includes cultivating an antibiotic A/16686 producing culture in an aqueous nutrient culture medium containing an assimilable source of carbon, an assimilable source of nitrogen and inorganic salts under the usual conditions known for the cultivation of Actinoplanes in general and for the A/16686 producing ones in particular (c.f. U.S. Pat. No. 4,303,646, cited above), and adding an effective amount of the appropriate precursor to selectively enhance the production of antibiotic A/16686 factor $A_2$ and/or factor $A_3$.

The appropriate precursor may be added to the fermentation in a continuous or discontinuous way during fermentation or may be added to the cultivation medium before fermentation. It may be added directly, if suitably fluid at the fermentation temperature, or it may be added as a solution, suspension or emulsion, and preferably it is an aqueous solution of suspension.

An "effective amount" of the appropriate precursor means an amount of precursor as defined above which, when added to the fermentation, gives a concentration of a selective precursor sufficient to produce the selective increase of the specific factor of antibiotic A/16686, without causing toxic effects to the growing culture of the producing microorganism.

The rate of addition of the precursor must be high enough to increase the yield of the desired factor to a considerable or optimum extent without however producing a toxic effect on the fermentation.

In general, it may be useful to feed an effective amount of the appropriate precursor in continuous or portionwise during the production stage of the fermentation.

Following fermentation, if desired, antibiotic A/16686 complex or the single factor $A_2$ or $A_3$ can be recovered according to the known procedures or obvious modifications thereof.

The nutrient fermentation media suitable for the fermentation of the A/16686 producing strain which can be used in the method of the invention, usually contain: a suitable carbon source which, for instance, may be selected from sugars (e.g. glucose, sucrose, maltose), polysaccharides (e.g. starch, dextrane) polyalcohols (e.g. glycerol, propylene glycol); suitable nitrogen sources which, for instance, may be selected from ammonium salts, asparagine, peanut meal, soybean meal, meat extract, tryptone, peptone, yeast hydrolyzate, yeast extract and corn step liquor; and inorganic salts. Among the inorganic salts which can be incorporated in the culture media there are the customary soluble salts capable of yielding sodium, potassium, iron, zinc, cobalt, magnesium, calcium, ammonium, chloride, carbonate, sulfate, phosphate, nitrate and the like ions.

Ordinarily, the antibiotic-producing strain is pre-cultured in a shake flask, then the culture is used to inoculate jar fermentors for production of substantial quantities of the antibiotic substances. The medium used for the pre-culture can be the same as that employed for larger fermentations, but other media can also be employed.

The fermentation is carried out for a time varying from 50 to 150 hours under submerged aerobic conditions at a temperature between 25° C. and 35° C., preferably between 27° C. and 33° C. The addition of the selectively effective amount of appropriate precursors can be made to the fermentative media before inoculation of the producing strain, however, it is preferably made 24 to 48 hours after the fermentation is started. The addition may be made in one or several portions or in a continuous way.

According to a typical experiment embodying this invention, a culture of the A/16686 producing strain, maintained on oat-meal agar slants, is inoculated into a flask containing 100 ml of a vegetative medium. After 36 hours, samples of the culture (5 milliliters) are used to inoculate a series of fermentation flasks containing 100 ml of fermentative medium. After 24 to 48 hours of fermentation, the selectively effective amount of precursor is added as appropriate. If concomitant increase of two factors of A/16686 complex is desired, the two appropriate precursors are added to the same fermentation flask. The fermentation is continued for additional 60 to 150 hours, then the fermentation cake is removed and samples of the broth are analyzed by HPLC.

The recovery of the antibiotic substances may be carried out as known in the art.

The antibiotics produced during fermentation of the strain Actinoplanes sp. ATCC 33076 are found mainly in the mycelial mass. A preferred method of recovering the A/16686 antibiotics is therefore, by extraction of the separated mycelium.

Extraction of the mycelial mass is best accomplished with methanol, but other lower alkanols and acetone are also suitable. The A/16686 antibiotics are recovered from the extracting solvent by routine procedures to give a mixture of the A/16686 antibiotics, the A/16686 complex. The A/16686 complex is further purified and then the individual factors are separated from each other. Separation of the A/16686 complex into the single components may be achieved by a variety of recognized methods which essentially involve chromatographic procedures. For optimum separation of factors reverse phase HPLC is preferred. In such HPLC separations, a preferred column is u-BONDAPAK® C18, trademark of Waters Company, and preferred mobile phases are mixtures of aqueous $HCOONH_4$ and $CH_3CN$ in variable ratios. For large scale separation of antibiotic A/16686 factor $A_2$, column chromatography is preferably employed. In such column separations, a preferred absorbent is AMBERLITE® XAD trademark of Rohm and Hass Co., and preferred solvent systems are mixtures of water and acetonitrile and mixtures of ammonium formiate and acetonitrile. Separation of minor factors $A_1$ and $A_3$ by column chromatography may be carried out but it requires subsequent column separation of enriched fractions. Again AMBERLITE® XAD trademark of Rohm and Hass Co., is a preferred absorbent mixtures of water and acetonitrile and mixtures of ammonium formiate and acetonitrile are the preferred solvent systems.

For veterinary application, the whole fermentation cake or concentrated broth can be used.

The addition of the precursor to the fermentation is such that it does not affect considerably its predetermined pH range. Thus, for instance, when free acid precursors are added directly to the medium, the pH is maintained under control by buffering the medium or by immediate neutralization with bases which are non-toxic to the microorganism.

When the precursor to be added is an aminoacid, it may be supplied to the fermentation as an aqueous solution of its salts with acids or bases which are non-toxic to the producing microorganism, e.g. hydrochlorides and sodium salts, even if in many instances the aminoacid may conveniently be added as a solution of the "internal salt". Both racemic mixtures and optically active isomers can be used as precursors.

However, in general, the addition of the L-form gives higher yields than the corresponding D-form.

The preferred embodiment of the process of this invention is therefore represented by the use of the L-form of the aminoacid precursor for enhancing the concentration of factor $A_3$ (L-valine, a salt or an ester thereof), and/or factor $A_2$ (L-leucine, a salt or an ester thereof) of antibiotic A/16686 complex. According to this preferred embodiment, it is also possible to increase the percentage of factor $A_2$ in the fermentation product over 80% of the complex.

With lower alkanoic acid precursors (isobutyric acid, isovaleric acid, alpha-keto-isovaleric acid, and alpha-keto-isocaproic acid) the addition may be made through an aqueous solution of their salts with non-toxic bases; ammonium and sodium salts are usually preferred.

When esters of the above lower alkanoic acids and unsaturated fatty acids with mono-hydroxy lower alkanols are employed as precursors, said esters are usually derived from methanol, ethanol and propanol, although esters with $C_4$–$C_6$ alkanols may also be employed. In this case, the $C_4$–$C_6$ alkanol must be different from that which may act as precursor for the other factor, (isobutanol or isoamyl alcohol), unless concomitant increase of the other factor is desired.

Alkanol precursors such as isobutanol and isoamyl alcohol are usually added as such to the fermentation. However, they can be supplied also as esters of acids which are non-toxic to the microorganism. These acids must be different from those which may act as precursors for the other A/16686 factor unless concomitant increase of the other factor is desired. Usually, esters with linear ($C_2$–$C_4$) alkanoic acids such as acetic, propionic and butyric acid are preferred.

The "selectively effective amount" to be added to the fermentation medium according to this invention depends on the type of precursor. Usually, with the esters of the lower alkanoic acids (isobutyric acid, isovaleric acid) amounts that yield a concentration of the acid into the fermentation medium ranging between 0.1. g/l and 5 g/l are employed, with the range between 0.1 g/l and 1 g/l being preferred. With lower alkanols (isobutanol, isoamyl alcohol) or their esters with acids which are non-toxic to the microorganism, amounts that yield a concentration of the alcohol ranging between 0.5 g/l and 5 g/l are usually employed, with the range between 1 g/l and 2 g/l being preferred.

With the aminoacids (valine, leucine) and the keto-acids (alpha-keto-isovaleric acid, alpha-keto-isocaproic acid) or their salts with acids and bases the "selectively effective amount" added to the fermentation medium usually ranges between 0.2 g/l and 5 g/l, and preferably between 0.5 g/l and 4 g/l; the most preferred range being between 2 and 4 g/l.

In the case where the lower alkanoic acids (e.g. isobutyric acid, isovaleric acid), or their salts are directly added to the fermentation medium, the "selectively effective amount" usually ranges between 0.1 g/l and 2.5 g/l, with the range between 0.3 g/l and 1.5 g/l being preferred.

Concentrations higher than those indicated above may still be effective in enhancing the relative percentage of one of the A/16686 factors but, in general, the overall yield is depressed because of toxic effects on the culture.

A further object and preferred embodiment of the invention is represented by a method for enhancing the production of antibiotic A/16686 complex, antibiotic A/16686 factor $A_2$ or factor $A_3$ which comprises adding a butanoic acid derivative or precursor that can release butanoic acid under the fermentation conditions, to an A/16686 producing culture.

In fact, it has been surprisingly found that the selective enhancement of the production of an A/16686 factor according to the method of the invention is further increased if a butanoic acid derivative or precursor is added in conjunction with the appropriate precursor of an A/16686 factor.

Preferred examples of butanoic acid derivatives or precursors are ($C_1$–$C_6$) alkyl esters, mono- and poly-hydroxy alkyl esters.

Particularly preferred are ethyl butyrate and tri-butyrine.

When dealing with the addition of any substance to the fermentation medium and, in particular, when dealing with the addition of an appropriate precursor and butanoic acid or a derivative or precursor thereof, the term "in conjunction" encompasses the addition of the substances referred to simultaneously or sequentially (one after the other and vice versa) at an interval such that the combined effects of the added substances can still manifest themselves on the fermentation.

Obviously, the present definition encompasses also the case in which one or both substances added "in conjuction" have been previously added to the culture medium or are already present in it.

General, a butanoic acid derivative or precursor is added in an amount that yields a concentration of the acid in the fermentation medium from 0.5 g/l to 2 g/l.

The yields in antibiotic complex are in general considerably increased and when the proper precursor is also added, the percentage of the given antibiotic factor may be increased to about 95–98%.

Particularly preferred is a method for preparing antibiotic A/16686 factor $A_2$, with high yields and purity which comprises adding leucine, and most preferably L-leucine, in conjunction with tri-butyrine or ethyl butyrate to an A/16686 producing culture, during fermentation.

The following examples describe in further detail some specific embodiments of the method of the invention.

EXAMPLE 1

An oatmeal agar slant of Actinoplanes sp. ATCC 33076 is inoculated into a 500 ml flask containing 100 ml of the following vegetative medium (g/l):

| | |
|---|---|
| Soybean meal | 13 |
| Glucose | 12 |
| Starch | 13 |
| $CaCO_3$ | 4 |

After 36 hours on a rotary shaker at 28–30° C., 5 ml of the culture are used to inoculate 500 ml flasks containing 100 ml of the following fermentation medium (g/l):

| | |
|---|---|
| Soybean meal | 30 |
| Glycerol | 20 |
| Starch | 4 |
| Glucose | 4 |
| Maltose | 20 |
| Sucrose | 20 |
| $CaCO_3$ | 6 |

After cultivating at 28–30° C. on a rotary shaker for 24 hours, the appropriate precursor is added. After 90–96 hours of cultivation, the fermentation cake is removed by centrifuge and the broth is analyzed for its content in antibiotic A/16686 factors according to the following HPLC method:

a. Separation by gradient reverse phase partition

| | | |
|---|---|---|
| Instrument: | pump Varian 5000 A; | |
| | detector Varian at 254 micrometer; | |
| | injector: Rheodyne model 7125; | |
| | integrator: Spectra Physics model 4000; | |
| Column: | silanized silica gel; | |
| | Brownlee Lab. RP 18 Spheri 5 | |
| Mobile phase: | 0.05M $NaH_2PO_4$/acetonitrile, 65:35, pH 6 | |
| Flow rate: | 1.8 ml/min | |
| Injection: | 20 microliter | |
| Operative conditions: | Isocratic conditions | |
| Retention times: | A/16686 factor $A_1$ | 6.69 min |
| | A/16686 factor $A_2$ | 10.16 min |
| | A/16686 factor $A_3$ | 16.29 min |

B. Percentage distribution

The components are separated by the above procedure and their relative distribution is obtained as a percent of the total of the three peaks by the area percentage method. The results of representative experiments are reported below:

| Precursor additions (g/l) | Total yield Mg/1 | % Factor $A_1$ | % Factor $A_2$ | % Factor $A_3$ |
|---|---|---|---|---|
| None (—) | 102 | 16 | 67 | 17 |
| Valine 1 | 120 | 20 | 42 | 38 |
| Isobutyric acid 0.2 | 110 | 13 | 55 | 32 |
| Leucine | | | | |
| 0.5 | 103 | 11 | 82 | 7 |
| 1 | 130 | 12 | 84 | 4 |
| 2 | 250 | 6 | 92 | 2 |
| Isovaleric acid | | | | |
| 0.1 | 130 | 7 | 87 | 6 |
| 0.5 | 50 | 5 | 90 | 5 |
| Ethyl butyrate 0.5 | 280 | 19 | 67 | 14 |
| Tri-butyrine 0.5 | 390 | 21 | 61 | 18 |
| Leucine plus Tri-butyrine 0.5 + 1 | 502 | 9 | 84 | 7 |

We claim:

1. A process for preparing antibiotic A/16686 complex containing $A_2$ in an amount such that the percentage of $A_2$, is from about 82% to about 92% of the total of components $A_1$, $A_2$, $A_3$ and as measured chromatographically, which comprises the steps of:
   1) culturing Actinoplanes sp ATCC 33076 or an A/16686 producing mutant of Actinoplanes sp. ATCC 33076 in an aqueous nutrient culture medium containing 1) an assimilable source of carbon selected from sugars, polysaccharides or polyalcohols; 2) an assimilable source of nitrogen selected from ammnonium salts, asparagine, peanut meal, soybean meal, meat extract, tryptone, yeast hydrolyzate, yeast extract or corn steep liquor; and 3) inorganic salts under conditions capable of producing recoverable amounts of antibiotic A/16686 complex containing component $A_2$;
   2) adding to the culture medium an amount of a precursor wherein the amount is from about 0.1 g/l to about 5 g/l and the precursor is selected from the group consisting of leucine, the salts of leucine with bases which are nontoxic to the microorganism, isovaleric acid and isovaleric acid salts formed with bases which are non-toxic to the organism; and
   3) recovering the antibiotic A/6686 enriched in $A_2$ from the culture medium.

2. The process according to claim 1 wherein the salt is a sodium or ammonium salt.

3. The process according to claim 1 wherein the salt is a hydrochloride or sulfate salt.

4. The process according to claim 1 wherein the fermentation is carried out at a temperature between 25° C. and 35° C.

5. The process according to claim 1 wherein the addition of the precursor is carried out 24 to 48 hours after the fermentation is started.

6. A process according to claim 1 wherein the antibiotic A/16686 factor $A_2$ is separated from the antibiotic complex by extraction of the broth or the mycelium with polar organic solvents.

7. The process according to claim 6 wherein the antibiotic A/16686 complex enriched in $A_2$ is isolated from the culture medium by chromatographic techniques.

8. A process according to claim 1 wherein the antibiotic A/16686 factor $A_2$ is recovered from the antibiotic complex by extraction of the broth or the mycelium with polar organic solvents.

9. The process according to claim 8 wherein the antibiotic A/16686 complex enriched in $A_2$ is isolated from the culture medium by chromatographic techniques.

10. The process according to claim 1 wherein the precursor is leucine or a salt of leucine.

11. The process according to claim 10 wherein the leucine is L-leucine.

12. The process according to claim 10 wherein the amount of precursor ranges between 0.2 g/l and 5 g/l.

13. The process according to claim 10 wherein the salt is a sodium or ammonium salt.

14. The process according to claim 10 wherein the salt is a hydrochloride or sulfate salt.

15. The process according to claim 1 wherein the precursor is isovaleric acid or a salt of isovaleric acid.

16. The process according to claim 15 wherein the amount of precursor ranges between 0.1 g/l and 2.5 g/l.

17. The process according to claim 15 wherein the salt is a sodium or ammonium salt.

18. The process according to claim 15 wherein the salt is a hydrochloride or sulfate salt.

19. A process for preparing antibiotic A/16686 complex containing $A_3$ in an amount such that the percentage of $A_3$ is from about 32% to about 38% of the total of components $A_1$, $A_2$, $A_3$ as measured chromatographically, which comprises the steps of:
   1) culturing Actinoplanes sp ATCC 33076 or an A/16686 producing mutant of Actinoplanes sp. ATCC 33076, in an aqueous nutrient culture medium containing 1) an assimilable source of carbon selected from sugars, polysaccharides or polyalcohols; 2) an assimilable source of nitrogen selected from ammonium salts, asparagine, peanut meal, soybean meal, meat extract, tryptone, yeast hydrolyzate, yeast extract or corn steep liquor; and 3) inorganic salts under conditions capable of producing recoverable amounts of antibiotic A/16686 complex containing component $A_3$;
   2) adding to the culture medium an amount of a precursor wherein the amount is from about 0.1 g/l to about 5 g/l and the precursor is selected from the group consisting of valine, the salts of valine with bases which are nontoxic to the microorganism, isobutyric acid, and isobutyric acid salts formed with bases which are non-toxic to the organism; and
   3) recovering the antibiotic A/16686 enriched in $A_3$ from the culture medium.

20. The process according to claim 19 wherein the salt is a sodium or ammonium salt.

21. The process according to claim 19 wherein the salt is a hydrochloride or sulfate salt.

22. The process according to claim 19 wherein the fermentation is carried out at a temperature between 25° C. and 35° C.

23. The process according to claim 19 wherein the addition of the precursor is carried out 24 to 48 hours after the fermentation is started.

24. A process according to claim 19 wherein the antibiotic A/16686 factor $A_3$ is separated from the antibiotic complex by extraction of the broth or the mycelium with polar organic solvents.

25. The process according to claim 24 wherein the antibiotic A/16686 complex enriched in $A_2$ is isolated from the culture medium by chromatographic techniques.

26. A process according to claim 19 wherein the antibiotic A/16686 factor $A_3$ is recovered from the antibiotic complex by extraction of the broth or the mycelium with polar organic solvents.

27. The process according to claim 26 wherein the antibiotic A/16686 complex enriched in $A_2$ is isolated from the culture medium by chromatographic techniques.

28. The process according to claim 19 wherein the precursor is isobutyric acid or a salt of isobutyric acid.

29. The process according to claim 28 wherein the amount of precursor ranges between 0.1 g/l and 2.5 g/l.

30. The process according to claim 28 wherein the salt is a sodium or ammonium salt.

31. The process according to claim 28 wherein the salt is a hydrochloride or sulfate salt.

32. The process according to claim 19 wherein the precursor is valine or a salt of valine.

33. The process according to claim 32 wherein the valine is L-valine.

34. The process according to claim 32 wherein the amount of precursor ranges between 0.2 g/l and 5 g/l.

35. The process according to claim 32 wherein the salt is a sodium or ammonium salt.

36. The process according to claim 32 wherein the salt is a hydrochloride or sulfate salt.

* * * * *